United States Patent [19]

Schonfeld

[11] 4,140,115
[45] Feb. 20, 1979

[54] PRESSURE SENSITIVE ADHESIVE COMPOSITIONS FOR COATING ARTICLES TO BE ATTACHED TO SKIN

[75] Inventor: Edward Schonfeld, New York, N.Y.

[73] Assignee: Johnson & Johnson, New Brunswick, N.J.

[21] Appl. No.: 580,371

[22] Filed: May 23, 1975

Related U.S. Application Data

[63] Continuation-in-part of Ser. No. 421,457, Dec. 3, 1973, abandoned, which is a continuation-in-part of Ser. No. 277,435, Aug. 2, 1972, abandoned.

[51] Int. Cl.$^2$ .................. A61F 13/00; A61L 15/00
[52] U.S. Cl. ...................................... 128/156; 428/411
[58] Field of Search ........ 427/207; 428/261, 343–356, 428/411

[56] References Cited

U.S. PATENT DOCUMENTS

| | | | |
|---|---|---|---|
| 3,121,021 | 2/1964 | Copeland | 427/207 UX |
| 3,152,940 | 10/1964 | Abel et al. | 427/207 UX |
| 3,632,740 | 1/1972 | Robinson et al. | 427/207 UX |
| 3,740,414 | 6/1973 | Olson | 427/207 UX |

*Primary Examiner*—Bernard D. Pianalto
*Attorney, Agent, or Firm*—Steven P. Berman

[57] ABSTRACT

Skin damage, i.e., the stripping of tissue cells from the stratum corneum, caused by removal of a backing material which has been held in adherent contact with a skin surface by means of a pressure sensitive adhesive composition coated on the backing material, is markedly reduced by incorporation of about 4 to 20% by weight of an unreacted polyol uniformly dispersed in the water-insoluble pressure sensitive adhesive mass. Suitable polyols include polyethylene glycol and polypropylene sorbitol monolaurate. This improved mass finds special application for use in conjunction with adhesive bandages or rolled tapes composed of a backing material of a plasticized film of polyvinyl chloride. Remarkably, the reduction in skin damage is accomplished without sacrificing low mass transfer to skin upon removal of the backing material, cohesive strength, adhesion, or wearability, all of which are highly desirable properties of pressure sensitive adhesive tapes and bandages.

14 Claims, No Drawings

PRESSURE SENSITIVE ADHESIVE COMPOSITIONS FOR COATING ARTICLES TO BE ATTACHED TO SKIN

BACKGROUND OF THE INVENTION

This application is a continuation-in-part of my copending application, Ser. No. 421,457, filed Dec. 3, 1973, which is a continuation-in-part of my copending application, Ser. No. 277,435, filed Aug. 2, 1972, both now abandoned.

This invention relates to adhesive articles comprising a backing material and a water-insoluble pressure sensitive adhesive composition coated upon at least one surface of the backing material for attaching it by means of the pressure sensitive adhesive coating to human skin. This invention is especially concerned with the reduction of skin damage by providing a backing material, e.g. a plasticized film backing having a water-insoluble pressure sensitive adhesive composition coated thereon which composition includes from about 4 to 20% by weight of an unreacted polyol uniformly dispersed therein.

Backing materials that are intended for attachment to skin by means of a pressure sensitive adhesive coating include the well-known plasticized polyvinyl chloride film backings which have achieved considerable commercial success as adhesive tapes and bandages. Other such backing materials include woven and nonwoven fabrics, paper and metallic foil bodies, as well as foamed materials such as, for example, foamed polyurethane.

When pressure sensitive adhesive backing materials are repeatedly applied, removed and re-applied to the same area of the skin, there occurs some stripping of the cells of the epidermal layer known as the stratum corneum. These skin cells, while occluded, become macerated and, as the adhesive coated article is removed, the macerated cells adhere to the adhesive mass of the article. Stripping away of these cells of the stratum corneum is herein referred to by the term "skin damage". Such skin damage is not serious when a pressure sensitive coated article, e.g., a bandage, is worn only for a relatively short time. But when the bandage is repeatedly applied to and removed from the same area of skin surface, as in changing a dressing, sufficient cells can be stripped away to result in localized erythema.

Although skin damage occurs to some degree with any backing material that is attached to the skin by means of a pressure sensitive adhesive, it is, however, more noticeably a problem with those backing materials that comprise a plasticized plastic film, e.g., a plasticized polyvinyl chloride film.

While such skin damage can be detected by gross observation, it can best be measured quantitatively by determining the amount of transepidermal water loss (TWL) from the skin surface involved. It has been found that the quantitative measure of the TWL correlates very well with skin damage. This is because the erosion of cells from the stratum corneum removes a portion of the protective layer thus permitting increased transpiration of water through the epidermal layers. Such correlation of TWL and skin damage is referred to in *Surgical Dressings and Wound Healing*, K. J. Harkiss, Editor, Bradford University Press, London (1971) on pages 144 through 146.

The problem of skin damage is well recognized in the art and there have been repeated attempts to alleviate such damage by modification of the compositions of the pressure sensitive adhesives, all without success. In fact, many modified adhesive formulations result in increased skin irritation. Furthermore, any modification of a pressure sensitive adhesive composition must, in order to be regarded as successful in the reduction of skin damage, accomplish that result without detriment to either adhesive strength or some other highly desirable characteristic of the adhesive. An improvement of one property at the expense of some other valued property is in actuality no improvement. For example, a reduction in adhesive strength will consequently reduce skin damage since the adhesive adheres less tenaciously to the skin, and causes fewer cells to be stripped from the area contacted upon removal of the bandage. Because the bandage has a lower level of adhesion, inferior wear properties result which are unacceptable, and there is no net gain in improvement. Still further, in attempting to modify the pressure sensitive adhesive compositions, one must take precaution not to include in such compositions, materials which are known to have adverse effects on the skin, for example, monomeric amines and the like.

Hence, the primary object of this invention is to provide a water-insoluble pressure sensitive adhesive composition which, when utilized to attach an article to human skin, markedly reduces skin damage.

A still further object of this invention is to provide a bandage which incorporates in its adhesive mass an additive physically dispersed therein which achieves a remarkable reduction in skin damage, but not at the expense of other highly desirable properties of such heretofore known adhesive tapes and bandages.

SUMMARY OF THE INVENTION

It has now been discovered that the foregoing objects and advantages, as well as other objects and advantages which will become apparent upon further reading of this specification, are met by including an unreacted polyol uniformly dispersed in the water-insoluble pressure sensitive adhesive composition used to coat the article for adherent application to skin. Such water-insoluble pressure sensitive coatings are well known in the art and are collectively referred to by the term "adhesive mass." It is necessary that such pressure sensitive adhesive compositions be water-insoluble in order to prevent their peeling when they come in contact with water. Thus, water-soluble adhesive compositions would not result in effective adhesive bandages and tapes due to such peeling upon contact with water and would therefore not be useful or desirable in the present invention.

A pressure sensitive adhesive sheet for use as tape, bandages, corn pads or the like comprises a backing material such as one of the backing materials heretofore set forth, and a suitable water-insoluble pressure sensitive adhesive which is based either on a rubber or an acrylic composition. Either of these mass compositions can satisfactorily include the polyols in the manner of this invention to achieve the objects of this invention.

DETAILED DESCRIPTION OF THE INVENTION

Adhesive masses based on rubber elastomers include both natural rubbers such as pale crepe rubber or synthetic rubbers such as polyisobutylene or butyl rubber. The rubber is tackified with a tackifying agent such as polyterpene resin, e.g., poly-β-pinene, a natural resin, or rosin acid esters, such esters being with mono or polyhydric alcohols, as well as similar materials wherein the rosin group has been modified by hydrogenation. These adhesive masses, based on rubber elastomers, can also include inorganic or organic fillers such as zinc oxide, titanium oxide, aluminum oxide, calcium carbonate, starch and like material in finely divided or powdery form. In addition, such masses can also contain mineral oil or lanolin, together with various antioxidants such as, for example, alkylated diphenyl amines. In addition, there can be included a plasticizer such as alkylphthalates, alkyl adipates, and the like where the alkyl group is from $C_4$ to $C_{10}$ carbon atoms and also alkyl acetyl ricinoleate wherein the alkyl group is from $C_1$ to $C_{10}$ carbon atoms.

Although the adhesive masses based on rubber elastomers which include a polyol, according to the teachings of this invention, are quite satisfactory insofar as reduction of skin damage is concerned, the preferred adhesive masses are based on acrylic systems. Such acrylate masses are based upon an adhesive polymer of monomers which consists essentially of a major amount of a medium chain length alkyl acrylate monomer and preferably minor amounts of cohesion-inducing short chain monomers, plus a very small amount of an alkoxy silyl cross-linking monomer polymerizable in the acrylate system.

The medium chain length alkyl acrylate monomers of this invention generally are those averaging about 4–12 carbon atoms in the alcohol moiety and include: butyl, hexyl, 2 ethylhexyl, octyl, decyl, and dodecyl acrylates and the like, alone or in combination with one another or with higher and lower alkyl acrylates. The medium chain length acrylate monomer is present in the adhesive copolymer of this invention in a major amount by weight of the total monomers, preferably in the amount of about 55–85 parts by weight of the monomers. When the term "parts" is used above and hereinafter in this application, it shall mean parts per 100 parts by weight of the total monomer solids, unless otherwise indicated.

The cohesion-inducing short chain monomers of this invention generally are selected from vinyl acetate, methyl acrylate, acrylic acid, diacetoneacrylamide, N-t-butylacrylamide, and the like, and preferably are present in the total monomers in the amount of about 10–30 parts, preferably above about 15 parts.

The alkoxy silyl cross-linking monomer of this invention may be prepared as described in U.S. Patent application Ser. No. 399,837 filed Sept. 28, 1964, and comprises an alkoxy silyl alkyl group and an unsaturated functional terminal group copolymerizable with the other monomers. This functional terminal group preferably is an acrylate or substituted acrylate group such as

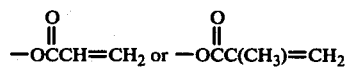

The polymerizable cross-linking alkoxy silyl alkyl groups found to be particularly effective are those having the general formula

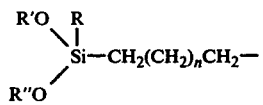

where R' and R" are either $CH_3$ or $CH_3CH_2$ and R is one of the group consisting of $CH_3$, $CH_2$, $CH_3O$ and $CH_3CH_2O$ and $n$ is a number of 0 through 8. A preferred silyl cross-linking monomer is 3-methacryloxypropyltrimethoxy silane, i.e.,

The amount of the silyl cross-linking monomer to be included in the copolymer depends on the exact constituents of the copolymer and the degree of cross-linking desired. Very small amounts are found to be effective. The silyl cross-linking monomer will generally be included in amounts of about 0.005 to 0.1 or 0.2 or more by weight of the total monomers with about 0.01 – 0.05 parts being preferred.

The polyol of this invention is physically incorporated in the adhesive mass in a quantity range from about 4 to 20% by weight based upon the total weight of the adhesive mass, and in preferred embodiments, about 9 to 13% by weight since this amount achieves adequate reduction of skin damage and the use of additional polyol (e.g., 14 to 20%) seems to result in an undesirable though tolerable softening of the adhesive mass. Such softening can lead under certain environmental conditions, such as high heat and humidity, to an undesirably excessive transfer of adhesive mass to the skin upon removal of the adhesive sheet.

The polyol can be blended or dispersed into the rubber or acrylate adhesive mass as a last step during the preparation of the adhesive mass or alternatively, it can be dispersed or blended with a previously prepared mass prior to applying the mass to the backing material. Generally, it is impractical to incorporate the polyol within a mass after the acrylate or rubber adhesive mass has been applied to the backing material.

The preferred procedure for incorporating or dispersing the polyol throughout the adhesive mass is to mix the polyol, at the desired weight percent, with the balance of the components comprising the adhesive mass prior to its being solvent coated, calendered or otherwise applied to the backing material.

In those adhesive masses based upon rubber elastomers which are, for example, conventionally blended in a Banbury mixer, the indicated amount of polyol is most advantageously added after blending of the other components of the adhesive mass has been completed. If a liquid component, such as for example, tricresyl phosphate is used as a softening agent as one component of the adhesive mass, the polyol is preferably dissolved or dispersed in this liquid, which then is added to the blend of the other ingredients of the adhesive mass and mixing continued until a uniform blend is obtained.

In those adhesive mass compositions based on an acrylate resin, it is the usual practice to employ a solvent coating technique in order to apply the adhesive mass to the article to be coated. In well known conventional techniques, an organic solvent, such as cyclohexane, is employed. The polyol is preferably dissolved or dispersed in such solvents and thoroughly blended into the adhesive mass just prior to applying the mass to the backing material.

The inclusion of the polyol in the adhesive mass of either a rubber based mass or an acrylic resin based mass does not alter the conventional techniques well known in the art for applying such masses to an article, such as a sheet material or film. Furthermore, the quantity of adhesive mass expressed in weight/surface area that is applied to the backing material is substantially the same as with presently known masses that do not include the polyol.

As referred to above, the backing material can be a plasticized film and may comprise a plasticized film backing of polyvinyl chloride, a copolymer of polyvinyl chloride and polyvinyl acetate, a copolymer of polyvinyl chloride and acrylonitrile and like self-supporting film materials as well as cloth and paper wherein such paper can be used alone or as carrier for a plasticized organosol.

Polyols which are suitable for inclusion in adhesive masses include the polyoxy-($C_2$-$C_4$)-alkylene glycols, the polyoxy-($C_2$-$C_4$)-alkylene sugars or sugar alcohols such as sorbitol and the $C_{12}$-$C_{18}$ fatty acid esters of polyoxy ($C_2$-$C_4$) alkylene sugars or sugar alcohols, such as polyoxy-ethylene sorbitol monolaurate. These polyol compounds preferably have a molecular weight in excess of 200 and can further be characteristic as having the structure

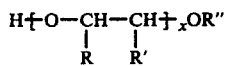

wherein $x$ is from about 4 to 20 and where R is H or $CH_3$, R' is H or —$CH_2$—$CH_2$—, at least R or R' being H, and R" is H, a six carbon chain sugar or a sugar alcohol or a $C_{12}$-$C_{18}$ fatty acid ester of a six carbon chain sugar or a sugar alcohol. Examples of such polyols include polyoxyethylene glycol; polyoxypropylene sorbitol monolaurate; polyoxypropylene sorbitol; polyoxybutylene glycol; polyoxyethylene sorbitol; polyoxyethylene sorbitol monolaurate; polyoxyethylene sorbitol monostearate; and polyoxypropylene mannose.

The preferred polyol is polyoxyethylene glycol having a number average molecular weight of about 400 (Carbowax 400, Union Carbide Co.)

Now having described the invention, the following examples are set forth by way of illustration.

EXAMPLE I

Eight separate batches, denoted A through H, are prepared each consisting of a mixture of 120 g. of 2-ethylhexyl acrylate, 50 g. of vinyl acetate, 30 g. of N-t-butylacrylamide, 0.07 g. of 3-(trimethoxysilyl)-propyl methacrylate and 200 g. of cyclohexane. Each batch is heated to reflux under nitrogen, 0.6 g. benzoyl peroxide is added, and the reaction mixture refluxed 4 hours. The viscous solution is then diluted by stirring in an additional 100 g. of cyclohexane and the reaction mixture cooled.

To each of the respective batches, A through H, is added 0.1 g. dioctyl tin maleate (Thermolite 813 — M&T Chemicals Co.) together with the additives set forth below. In order to achieve proper dispersion of the added components, they are premixed with a small quantity (e.g., 30 ml) of isopropanol before adding to the batch.

| Batch | Additive | |
|---|---|---|
| A | None | |
| B | 50g. polyoxyethylene | (20)* sorbitol monolaurate (Tween 20 SD Atlas Chemical Industries) |
| C | 50g. polyoxypropylene | (12)* sorbitol (G-2451 Atlas Chemical Industries) |
| D | 10g. polyoxyethylene | (8)* glycol (Carbowax 400 Union Carbide) |
| E | 20g. polyoxyethylene | (8)* glycol (Carbowax 400 Union Carbide) |
| F | 30g. polyoxyethylene | (8)* glycol (Carbowax 400 Union Carbide) |
| G | 40g. polyoxyethylene | (8)* glycol (Carbowax 400 Union Carbide) |
| H | 50g. polyoxyethylene | (8)* glycol (Carbowax 400 Union Carbide) |

*the number refers to the number average of ethyleneoxide units.

Each adhesive was then solvent coated in a conventional manner to provide 1 oz/yd² of adhesive on a film backing material having the following composition:

| | Parts |
|---|---|
| Polyvinyl chloride | 100 |
| Plasticizer | 66 |
| Stabilizer | 3.3 |

The coated tape is then cured by heating in an oven at 340° F. for 2 minutes.

To ascertain any differences in skin damage, 1×3 inch samples of each of the six tapes were applied to the backs of human volunteer subjects. Each day for 7 days the tapes were removed and reapplied. On days 1, 2, 3, 4 and 7 visual observations of skin damage were noted. The results are tabulated below.

| Tape With | Percent Polyol In Mass | Visual Determination Of Skin Damage |
|---|---|---|
| Mass A | 0 | Severe |
| Mass D | 4.8 | Moderate |
| Mass E | 9.1 | Moderate |
| Mass F | 13.0 | Very little |
| Mass G | 16.7 | Very little |
| Mass H | 20.0 | Very little |

Samples of each of the tapes were placed on the backs of eight subjects and changed daily for 7 days. Transepidermal water loss readings were taken on the tape covered areas and on a normal skin site on days 4 and 7 of the test period. The mean (actual amount of skin damage) figures are reported below.

| | TWL, mg/cm²/hour | |
|---|---|---|
| Tape With | 4th day | 7th day |
| Mass A | 1.82 | 3.63 |
| Mass B | 0.32 | 0.39 |
| Mass C | 0.25 | 0.34 |
| Mass H | 0.20 | 0.24 |

EXAMPLE II

Three separate batches of an adhesive mass having the composition 120 g. 2-ethylhexyl acrylate, 50 g. vinylacetate, 15 g. t-butylacrylamide, and 0.09 g. 3-(trimethoxysilyl)propyl methacrylate are prepared as in Example I, including the addition of the dioctyl tin maleate. To the first batch no polyoxyethylene glycol is added, to the second batch 20 g. of polyoxyethylene glycol (Carbowax 400) is added and to the third batch 30 g. of polyoxyethylene glycol (Carbowax 400) is added. The adhesive mass is applied in the usual manner to a polyvinyl film plasticized with an intermediate molecular weight polyester plasticizer, tricresyl phosphate, and stabilized with dibutyl tin maleate and Epoxy A-5. The Epoxy A-5 is a monomeric low molecular weight diepoxide formed by condensing epichlorohydrin with bisphenol-A. After application of the adhesive mass, the film is then cured as in Example I.

Bandages produced from this film were sterilized and tested for TWL at 4 and 7 days in the same manner as before, the results being reported below.

| Bandage | Mean TWL (mg/hr/cm$^2$) | |
|---|---|---|
| | 4th day | 7th day |
| Mass + 0 phr polyoxyethylene glycol | .98 | 4.03 |
| Mass + 10 phr polyoxyethylene glycol | .33 | .82 |
| Mass + 15 phr polyoxyethylene glycol | .45 | .57 |

These bandages were tested for the amount of force required for their removal from the skin of volunteer human subjects and it was found that there was no significant difference between the force required to remove the bandages from these subjects' skin, as set forth below:

| Mean Removal Force (grams) of Tapes Placed On Human Skin | |
|---|---|
| Tapes | Mean Force |
| Mass + 0 phr polyoxyethylene glycol | 162.5 |
| Mass + 10 phr polyoxyethylene glycol | 160.0 |
| Mass + 15 phr polyoxyethylene glycol | 145.0 |

These bandages in actual wear test conditions after 24 hours, have substantially identical wear properties.

EXAMPLE III

Two batches of the adhesive mass of Example II are prepared including 0 and 13% by weight respectively of polyoxyethylene glycol (Carbowax 600) having a number average molecular weight of 600. These separate batches are coated on the film backing set forth in Example II and cured.

EXAMPLE IV

Two batches of an adhesive mass having the formula

| 2-ethylhexyl acrylate | 70 parts |
|---|---|
| vinyl acetate | 30 parts |
| 3-(trimethoxysilyl)-propyl methacrylate | 0.02 parts | are prepared including 0% and 13% by weight polyoxyethylene glycol (Carbowax 400). These masses were likewise coated on the film backing set forth in Example II, and cured.

EXAMPLE V

Two batches of an adhesive mass having the formula

| 2-ethylhexyl acrylate | 60 parts |
|---|---|
| vinyl acetate | 25 parts |
| diacetone acrylamide | 15 parts |
| 3-(trimethoxysilyl)-propyl methacrylate | 0.045 parts | are prepared, including 0% and 13% polyoxyethylene glycol (Carbowax 400) respectively. These masses were likewise coated on the film backing set forth in Example II and cured.

EXAMPLE VI

Two batches of an adhesive composition comprising a blend of natural rubber and polyisobutylene tackified with a polyterpene resin are prepared. The first batch contained no polyoxyethylene glycol. The second batch contained 13% by weight of polyoxyethylene glycol (Carbowax 400). This batch was likewise coated on the film backing of Example II.

The tapes prepared in Examples III through VI are applied to the skin of human volunteer subjects and the TWL recorded after the 4th and 7th days. The results are reported below.

| Tape from Example | % Polyol | TWL (mg/hr/cm$^2$) Day | |
|---|---|---|---|
| | | 4th | 7th |
| III | 0 | 1.18 | 3.29 |
| | 13 | 0.81 | 2.46 |
| IV | 0 | 0.96 | 2.65 |
| | 13 | 0.66 | 2.34 |
| V | 0 | 0.70 | 4.59 |
| | 13 | 0.56 | 2.17 |
| VI | 0 | 1.12 | 3.95 |
| | 13 | 0.70 | 2.90 |

From the foregoing illustrative examples, it will be appreciated that the preferred polyol is polyoxyethylene glycol (Carbowax 400) employed at a concentration of 13% by weight dispersed in an adhesive mass coated upon a backing material.

It further can be appreciated that the inclusion of a polyol substantially reduces the degree of skin damage. The invention is not limited, however, to the specific embodiments set forth in the examples, and modifications or variations thereof, in light of the foregoing disclosure, will be apparent and are intended to be included within the scope of the appended claims.

What is claimed is:

1. An adhesive material for use on the skin which reduces the stripping of tissue cells upon removal comprising a backing having coated thereon a water-insoluble pressure sensitive adhesive mass, said mass having uniformly dispersed therein from 4 to 20% by weight of an unreacted polyol having the formula $$H \!\!-\!\!\left[\!O\!-\!\underset{R}{\overset{}{C}H}\!-\!\underset{R'}{\overset{}{C}H}\!\right]_{\!x}\!\!OR''$$

wherein $x$ is from about 4 to 20 and where R is H or CH$_3$, R' is H or —CH$_2$—CH$_2$—, at least R or R' being H, and R is H, a sugar, a sugar alcohol or a C$_{12}$–C$_{18}$ fatty acid ester of a sugar or a sugar alcohol.

2. An adhesive material according to claim 1 in which said sugar alcohol is sorbitol.

3. An adhesive material according to claim 1 in which said fatty acid ester is a sorbitol monolaurate.

4. An adhesive composition according to claim 1 in which said polyol comprises from about 9 to 13% by weight of said adhesive mass.

5. An adhesive material according to claim 1 in which said water-insoluble pressure sensitive adhesive mass comprises an acrylic resin.

6. An adhesive material according to claim 5 in which said acrylic resin is 2-ethylhexyl acrylate.

7. An adhesive material according to claim 5 in which said water-insoluble pressure sensitive adhesive comprises 2-ethylhexyl acrylate, vinyl acetate, and N-tert-butylacrylamide.

8. An adhesive material according to claim 1 in which said water-insoluble pressure sensitive adhesive mass comprises a rubber elastomer and a tackifier.

9. An adhesive material according to claim 1 in which said polyol is a polyoxyethylene glycol having a number average molecular weight of at least 200.

10. An adhesive material according to claim 1 in which said polyol is a polyoxy $C_2$-$C_4$ alkylene glycol having a number average molecular weight in excess of 200.

11. An adhesive material according to claim 9 in which said polyoxyethylene glycol has a number average molecular weight of 400.

12. An adhesive material according to claim 1 in which said backing is a film comprising plasticized polyvinyl chloride, and polyvinyl chloride copolymerize with a second monomer.

13. An adhesive material according to claim 1 in which said backing is a thin flexible plastic film.

14. An adhesive bandage for use on the skin which reduces the stripping of tissue cells upon removal comprising a backing having coated thereon a water-insoluble pressure sensitive adhesive mass, said mass having uniformly dispersed therein from 4 to 20% by weight of an unreacted polyol having the formula

wherein $x$ is from about 4 to 20 and where R is H or $CH_3$, R' is H or $+CH_2-CH_2+$, at least R or R' being H, and R is H, a sugar, a sugar alcohol or a $C_{12}$-$C_{18}$ fatty acid ester of a sugar or a sugar alcohol.

* * * * *